United States Patent [19]

Alaimo

[11] 4,393,208

[45] Jul. 12, 1983

[54] 5-METHYL-2-TRIFLUOROMETHYLIN-DOLO[2,3-B]QUINOXALINE

[75] Inventor: Robert J. Alaimo, Norwich, N.Y.

[73] Assignee: Norwich Eaton Pharmaceuticals, Inc., Norwich, N.Y.

[21] Appl. No.: 362,899

[22] Filed: Mar. 29, 1982

[51] Int. Cl.$^3$ ................. C07D 487/04; A61K 31/495
[52] U.S. Cl. ................................... 544/343; 424/250; 564/384
[58] Field of Search ......................................... 544/343

[56] References Cited

U.S. PATENT DOCUMENTS

| | | | |
|---|---|---|---|
| 2,215,859 | 9/1940 | Schepss et al. | 544/343 |
| 2,627,461 | 2/1953 | Friedman | 544/343 |
| 3,151,116 | 9/1965 | de Stevens et al. | 544/343 |

*Primary Examiner*—Donald G. Daus
*Assistant Examiner*—James H. Turnipseed
*Attorney, Agent, or Firm*—Anthony J. Franze

[57] ABSTRACT

The compound 5-methyl-2-trifluoromethylindolo[2,3-b]quinoxaline is useful as an immunomodulating agent.

1 Claim, No Drawings

5-METHYL-2-TRIFLUOROMETHYLINDOLO[2,3-b]QUINOXALINE

This invention is concerned with chemical compounds and more particularly with the compound 5-methyl-2-trifluoromethylindolo[2,3-b]quinoxaline useful as an immunomodulating agent.

An immunomodulating agent is a substance which regulates or otherwise affects the immune response of a host. Compounds having such capability are useful as drugs for mitigating the immunological incompetence of a host body often times encountered as an undesired side effect of cancer chemotherapy involving antineoplastic agents. Such depressed immune response lessens the protective function of the immune system permitting the invasion of pathogens such as viruses, bacteria and other parasites which otherwise could be resisted.

The compound of this invention exhibits salutary effect upon the immune system of an animal with respect to resistance to bacterial infection when such system has been depressed by administration of an antineoplastic. Thus, 75% or more of mice administered intraperitoneally 100 mg/kg of cyclophosphamide 4 days before being inoculated intravenously with $1 \times 10^5$ cells of *Pseudomonas aeruginosa* died. In mice not receiving cyclophosphamide, the mortality was about 40%. When the compound of this invention was administered at a level of 20 mg/kg intraperitoneally to cyclophosphamide (100 mg/kg) treated mice at days 4 and 2 before inoculation with *Pseudomonas aeruginosa*, there was a mortality of about 33%.

In order that this invention may be readily available to and understood by those skilled in the art, the currently preferred method for its preparation is set forth as follows:

A. N-Methyl-3-nitro-4-trifluoromethylbenzenamine

4-Chloro-3-nitrobenzotrifluoride (226 g., 0.1 mole) and ethanol (400 ml.) was treated with 40% methylamine (300 ml.) in small portions. The reaction was then warmed and finished addition dropwise. After the addition was complete, continued stirring mixture for 1 hr. The mixture stood overnight at room temperature. The reaction was stirred and chilled on an ice bath. The mixture was filtered and washed with 50% alcohol followed by hexane. The solid was dried at 60°. Yield 200 g. (91%). Material used in Part B without further purification.

B. 3-Amino-N-methyl-4-trifluoromethylbenzenamine

A mixture of N-methyl-3-nitro-4-trifluoromethylbenzenamine (20 g., 0.09 mole) and absolute alcohol (200 ml.) was reduced with 5% palladium on carbon 50% wet. The material absorbed 24 lbs. of hydrogen (100% theory) in 1 hr. The catalyst was removed by filtration and the filtrate stripped in vacuo. The dark oil crystallized to give 17 g. (99%). The material used as an intermediate in Part C.

C. 5-Methyl-2-trifluoromethylindole[2,3-b]quinoxaline

A mixture of 3-amino-N-metehyl-4-trifluoromethylbenzenamine (17 g., 0.09 mole) and isatin (13.2 g., 0.09 mole) with boric acid (14 g.) in glacial acetic acid (350 ml.) was stirred and heated at reflux for 2 hrs. The reaction mixture was stirred at room temperature overnight. The reaction mixture was filtered and the filtrate treated with water. A "brick red" solid precipitated. Yield 17 g. (63%).

An analytical sample was prepared by one recrystallization from alcohol, m.p. 208°.

Anal. Calc'd. for $C_{16}H_{10}F_3N_3$: C, 63.79; H, 3.35; N, 13.95. Found: C, 63.98; H, 3.38; N, 13.77.

What is claimed is:

1. The compound 5-methyl-2-trifluoromethylindolo[2,3-b]quinoxaline.

* * * * *